(12) United States Patent
Bormann et al.

(10) Patent No.: US 7,361,277 B2
(45) Date of Patent: Apr. 22, 2008

(54) BIOLOGICAL FLUID FILTER AND SYSTEM

(75) Inventors: Thomas J. Bormann, Melville, NY (US); Gerard DelGiacco, Yonkers, NY (US); Byron Selman, Huntington, NY (US)

(73) Assignee: Pall Corporation, East Hills, NY (US)

( * ) Notice: Subject to any disclaimer, the term of this patent is extended or adjusted under 35 U.S.C. 154(b) by 506 days.

(21) Appl. No.: 11/151,546

(22) Filed: Jun. 14, 2005

(65) Prior Publication Data

US 2005/0247627 A1 Nov. 10, 2005

Related U.S. Application Data

(62) Division of application No. 09/936,732, filed as application No. PCT/US00/06829 on Mar. 15, 2000, now Pat. No. 6,945,411.

(60) Provisional application No. 60/124,580, filed on Mar. 16, 1999.

(51) Int. Cl.
*B01D 69/02* (2006.01)
*B01D 61/14* (2006.01)
*B01D 69/06* (2006.01)
*B01D 63/00* (2006.01)

(52) U.S. Cl. ............... 210/645; 210/649; 210/650; 210/651; 210/767; 210/503; 210/500.27; 210/500.35; 210/500.37; 604/126; 604/406

(58) Field of Classification Search ............ None
See application file for complete search history.

(56) References Cited

U.S. PATENT DOCUMENTS

| | | | |
|---|---|---|---|
| 4,507,119 A | 3/1985 | Spencer | |
| 4,737,214 A | 4/1988 | Leurink et al. | |
| 4,880,548 A | 11/1989 | Pall et al. | |
| 4,913,756 A | 4/1990 | Shaposka et al. | |
| 4,923,620 A | 5/1990 | Pall | |
| 4,925,572 A | 5/1990 | Pall | |
| 5,100,564 A | 3/1992 | Pall et al. | |
| 5,152,905 A | 10/1992 | Pall et al. | |
| 5,229,012 A | 7/1993 | Pall et al. | |
| 5,258,127 A | 11/1993 | Gsell et al. | |
| 5,443,743 A | 8/1995 | Gsell | |
| 5,472,621 A | 12/1995 | Matkovich et al. | |
| 5,547,576 A | 8/1996 | Onishi et al. | |
| 5,679,264 A | 10/1997 | Gsell | |

FOREIGN PATENT DOCUMENTS

| | | |
|---|---|---|
| EP | 0 267 286 A1 | 5/1988 |
| EP | 0 606 646 A1 | 7/1994 |
| EP | 0 630 675 A1 | 12/1994 |
| WO | WO 91/04088 | 4/1991 |
| WO | WO 93/04763 | 3/1993 |
| WO | WO 96/03194 A1 | 2/1996 |

*Primary Examiner*—Krishnan S Menon
(74) *Attorney, Agent, or Firm*—Leydig, Voit & Mayer, Ltd.

(57) ABSTRACT

A filter device (100) comprising a filter (10) for producing a leukocyte-depleted plasma-rich fluid is disclosed.

10 Claims, 4 Drawing Sheets

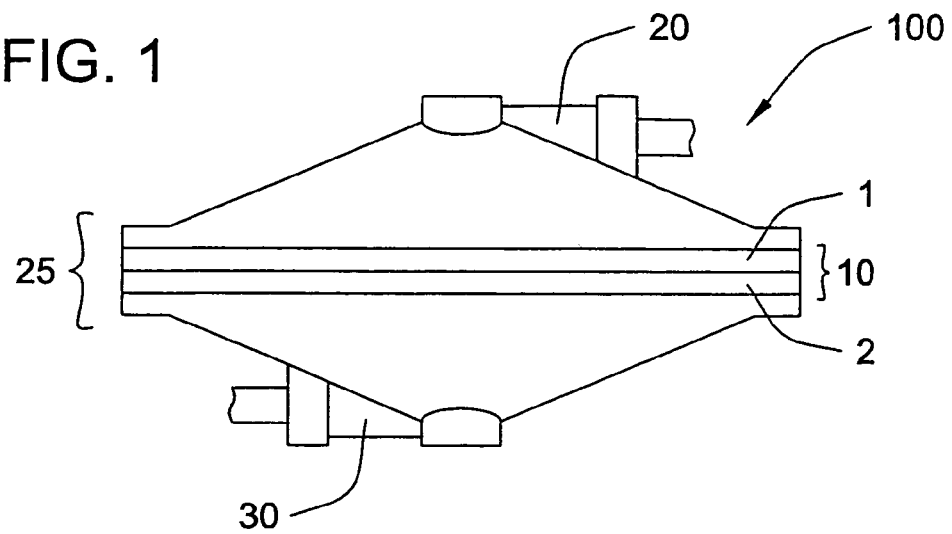
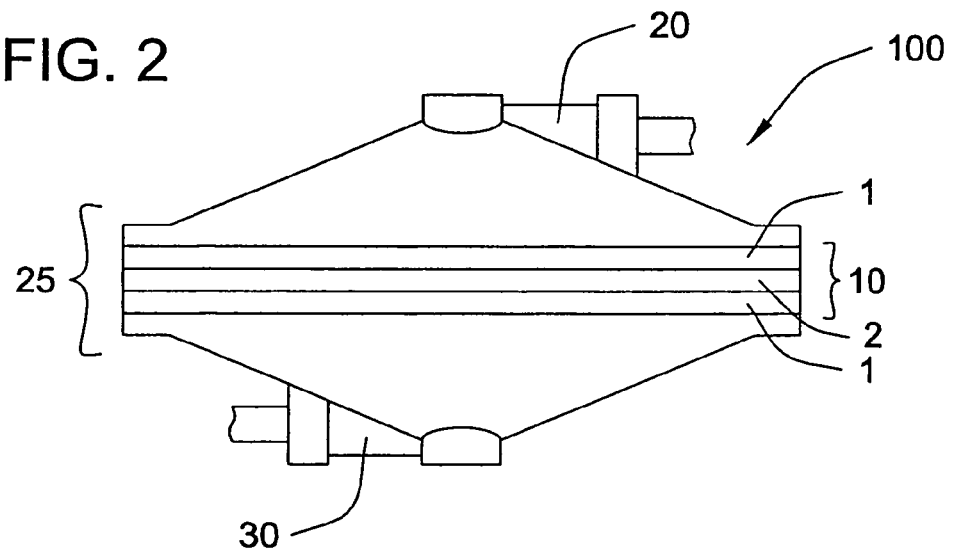
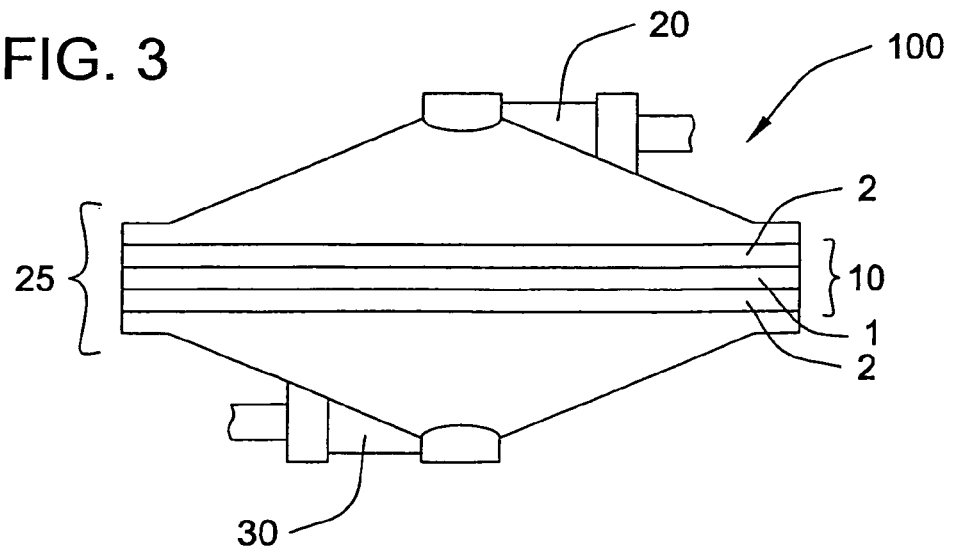

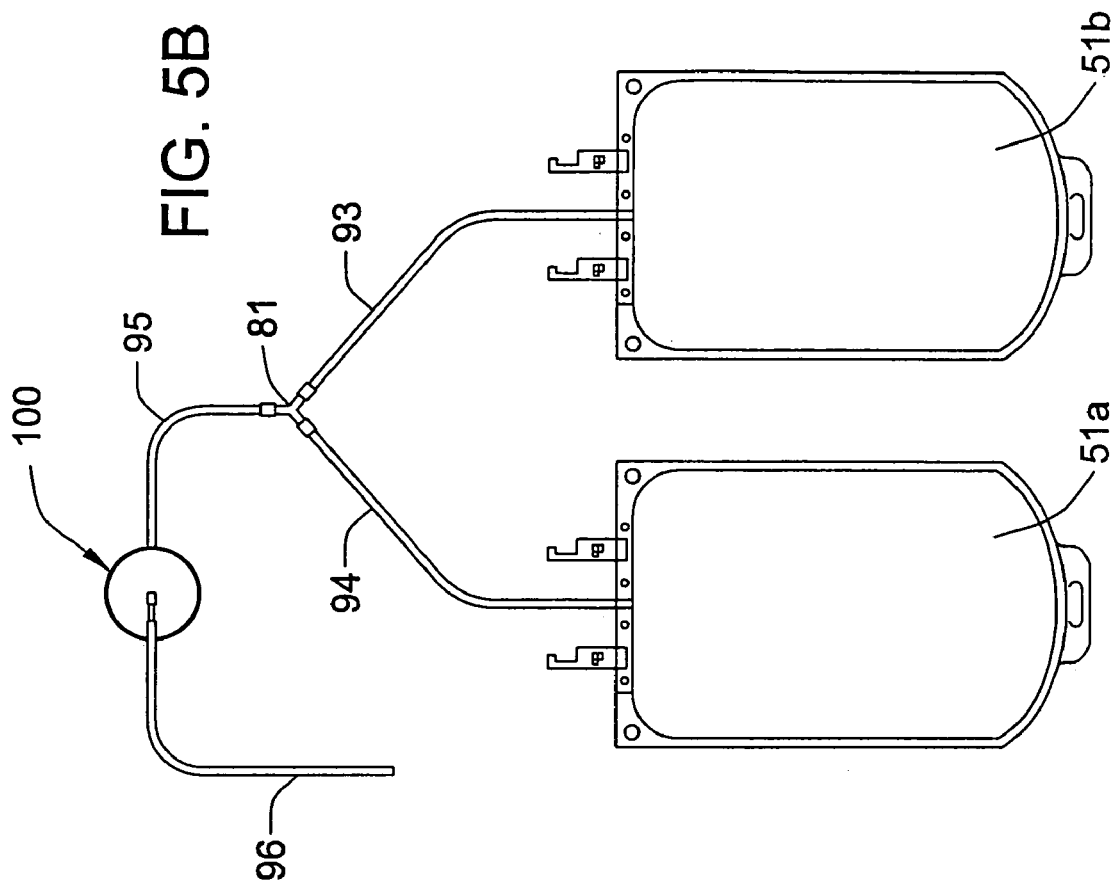
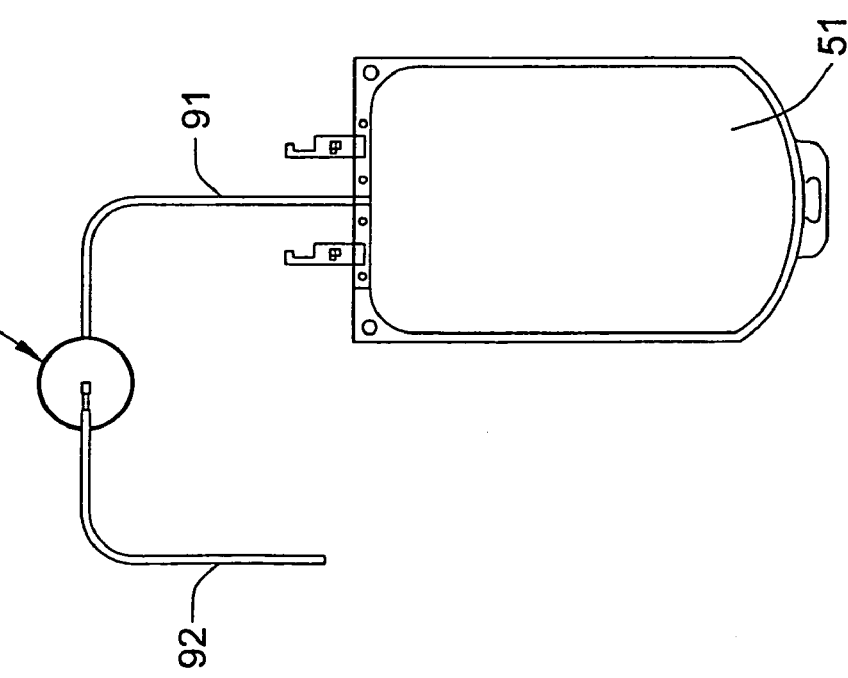

BIOLOGICAL FLUID FILTER AND SYSTEM

This application is a divisional of U.S. application Ser. No. 09/936,732, filed Dec. 20, 2001, which is a 35 U.S.C. §371 of PCT/US00/06829, filed Mar. 15, 2000. This application claims the benefit of U.S. provisional patent application 60/124,580, filed Mar. 16, 1999, which is incorporated by reference.

TECHNICAL FIELD

This invention relates to a filter for processing a biological fluid, more particularly, a filter that provides a leukocyte-depleted, substantially platelet-free biological fluid. Preferably, the filter provides a biological fluid that is substantially free of platelets, leukocytes, and biologically active complement fragments.

BACKGROUND OF THE INVENTION

Vertebrate blood contains a number of components, including plasma, platelets, and red blood cells. Blood also contains components such as various types of white blood cells (leukocytes), and proteins of the complement system, that provide for combating infection.

Blood components may be separated, and further processed, for a variety of uses, particularly as transfusion products. Illustratively, red blood cells (typically concentrated as packed red blood cells), plasma, and platelets (typically concentrated as platelet concentrate), can be separately administered to different patients. Some components, e.g., plasma and/or platelets, can be pooled before administration, and plasma can be fractionated to provide enriched components to treat disease.

While leukocytes combat infection and engulf and digest invading microorganisms and debris, the presence of leukocytes in transfusion products can be undesirable, since, for example, they may cause adverse effects (e.g., a febrile reaction) in the patient receiving the transfusion. Additionally, the presence of a significant level of red blood cells in some transfusion products (particularly if the transfusion products have been pooled) can lead to an adverse immune response by the patient.

The processing of blood to produce transfusion products can lead to the activation of the complement system, that acts on its own and in cooperation with antibodies in defending the host against infection. The complement system is composed of a series of plasma-borne blood proteins (proenzymes) that are sequentially activated in a series of reactions. The proteins are activated in cascade fashion, i.e., the output of one reaction is the input for the next. The cascade ultimately generates a terminal five-protein membrane attack complex (MAC, C5b-9), whose physiological function is protection of the host from invading microorganisms. The MAC causes lysis of the microorganisms.

While the complement system is generally beneficial in protecting the host, the presence of the various activated or activatable blood proteins (and fragments thereof) can be undesirable, particularly when these proteins and/or fragments are present in blood or blood components used for transfusion. For example, activation can lead to the administration of biologically active complement fragments such as C3a and its metabolite, C3a des Arg[77]. Transfusing activated complement into a patient can cause adverse affects such as anaphylactoid reactions, platelet aggregation, and/or immune suppression.

Accordingly, there is a need in the art for a filter for use with biological fluids such as blood and blood components, particularly for the production of plasma-rich blood products, that minimizes the contamination of the plasma-rich blood product by leukocytes, as well by other materials such as platelets and/or red blood cells. There is also a need for a filter that depletes complement and/or prevents the activation of complement in biological fluids such as plasma-rich blood products. These and other advantages of the present invention will be apparent from the description as set forth below.

SUMMARY OF THE INVENTION

In accordance with an embodiment of the invention, a filter device for providing a plasma-rich biological fluid substantially free of leukocytes comprises a filter including a first filter element and a second filter element, wherein the first filter element comprises a porous fibrous leukocyte depletion medium having a first predetermined critical wetting surface tension (CWST), and the second filter element, arranged downstream of the first filter element, comprises a porous fibrous leukocyte depletion medium having a second predetermined CWST. Typically, the CWST of the first element differs from the CWST of the second element.

In accordance with another embodiment of the invention, a filter for processing a biological fluid is provided comprising at least one filter element, wherein at least a portion of the surface of the element is aminated and hydroxylated relative to its bulk, or a portion of the surface of the element is aminated, and another portion of the surface of the element is hydroxylated, relative to the element's bulk.

In some embodiments, a filter according to the invention comprises at least two filter elements, wherein the surface of one filter element has a nitrogen-to-oxygen ratio in the range of from at least 0.01 to less than about 1.00 and/or the surface of the element is aminated relative to its bulk, and the surface of the other filter element is hydroxylated relative to its bulk. In one embodiment, one filter element has a CWST that differs from the CWST of the other element.

In preferred embodiments, the filter allows plasma-rich biological fluid to pass therethrough and substantially prevent the passage of leukocytes and platelets. In some embodiments, the filter substantially removes at least one biologically active complement fragment such as C3a and/or the filter does not substantially activate the fragment(s).

Methods for using the filter, the filter device, and systems including the filter device are also provided.

BRIEF DESCRIPTION OF THE DRAWINGS

FIG. 1 is an embodiment of a filter device according to the present invention.

FIG. 2 is another embodiment of a filter device according to the present invention.

FIG. 3 is another embodiment of a filter device according to the present invention.

FIG. 5 (A and B) illustrates other embodiments of biological fluid processing systems including a filter device according to the invention.

SPECIFIC DESCRIPTION OF THE INVENTION

Figure 4:
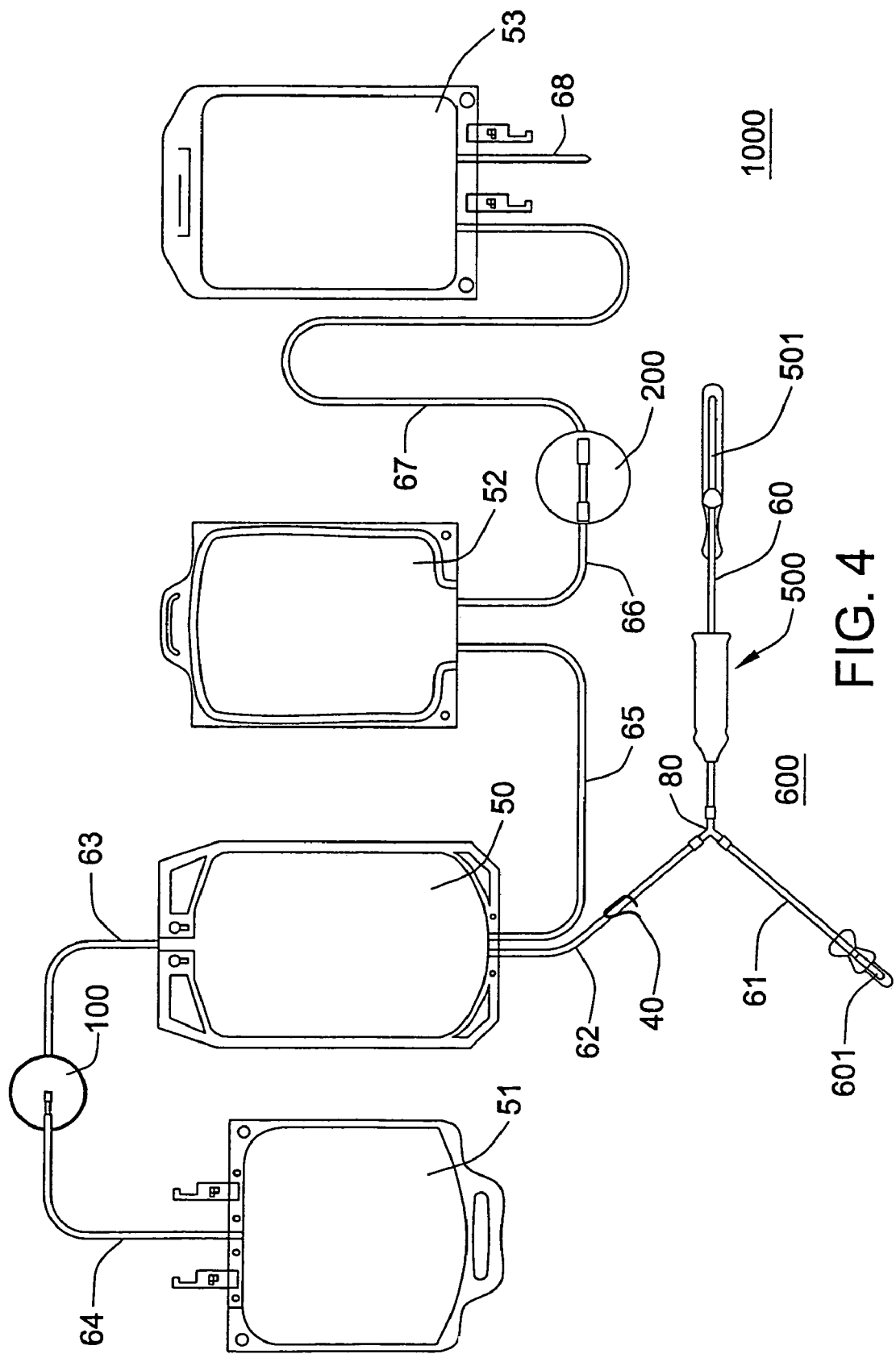
FIG. 4 is an embodiment of a biological fluid processing system including a filter device according to the invention.

In accordance with an embodiment of the present invention, a filter device for processing a biological fluid comprises a housing having an inlet and an outlet and defining a fluid flow path between the inlet and the outlet, a filter disposed in the housing across the fluid flow path, the filter comprising at least one filter element comprising a porous fibrous leukocyte depletion medium having a first predetermined critical wetting surface tension (CWST), and at least one filter element comprising a porous fibrous leukocyte and platelet depletion medium having a second predetermined CWST, wherein the filter is arranged to allow plasma to pass therethrough and substantially prevent the passage of leukocytes therethrough.

A filter device for processing a biological fluid in accordance with another embodiment of the invention comprises a housing having an inlet and an outlet and defining a fluid flow path between the inlet and the outlet, a filter disposed in the housing across the fluid flow path, the filter comprising at least one filter element comprising a porous fibrous leukocyte depletion medium having a first predetermined CWST, and at least one filter element comprising a porous fibrous leukocyte and platelet depletion medium having a second predetermined CWST, wherein the filter is arranged to allow plasma to pass therethrough and substantially prevent the passage of leukocytes therethrough, without substantially activating C3a in the biological fluid.

In accordance with another embodiment of the invention, a filter device for processing a biological fluid comprises a housing having an inlet and an outlet and defining a fluid flow path between the inlet and the outlet, a filter disposed in the housing across the fluid flow path, the filter comprising at least one filter element comprising a porous fibrous leukocyte depletion medium having a first predetermined CWST, and at least one filter element comprising a porous fibrous leukocyte and platelet depletion medium having a second predetermined CWST, wherein the filter is arranged to allow plasma to pass therethrough and substantially prevent the passage of platelets, leukocytes and C3a therethrough.

In another embodiment, a filter for processing a biological fluid comprises at least one filter element, preferably a fibrous element, wherein at least a portion of the surface of the element is aminated and hydroxylated relative to its bulk, or a portion of the surface of the element is aminated, and another portion of the surface of the element is hydroxylated, relative to the element's bulk.

In some embodiments, a filter according to the invention comprises at least two filter elements, wherein the surface of one filter element has a nitrogen-to-oxygen ratio in the range of from at least 0.01 to less than about 1.00 and/or the surface of the element is aminated relative to its bulk, and the surface of the other filter element is hydroxylated relative to its bulk.

Preferably, the filter includes at least one additional filter element, the filter element comprising any of the elements described above.

Embodiments providing leukocyte-depleted, substantially platelet-free biological fluid can be especially desirable, as potential disease-causing agents such as prions (implicated as causing disease, e.g., degenerative diseases such as Creutzfeld-Jacob disease (CJD) and "mad cow" disease) may attach to platelets and/or leukocytes, and the attached agents would be removed (and thus not transmitted to the patient during transfusion) upon removal of the leukocytes and the platelets.

A method for processing a biological fluid in accordance with an embodiment of the invention comprises passing a leukocyte-containing plasma-rich biological fluid through a filter device comprising a filter including a first element comprising a porous fibrous leukocyte depletion medium having a first predetermined CWST, and a second element comprising a porous fibrous leukocyte depletion medium having a second predetermined CWST, and collecting a filtered plasma-rich biological fluid substantially free of leukocytes.

A method for processing a biological fluid in accordance with another embodiment comprises passing a leukocyte-containing plasma-rich biological fluid through a filter device comprising a filter including at least one filter element, wherein at least a portion of the surface of the element is aminated and hydroxylated relative to its bulk, or a portion of the surface of the element is aminated, and another portion of the surface of the element is hydroxylated, relative to the element's bulk, and obtaining a filtered plasma-rich biological fluid substantially free of leukocytes and platelets.

In accordance with another embodiment, a method for processing a biological fluid comprises passing a leukocyte-containing plasma-rich biological fluid through a filter device comprising a filter including at least two filter elements, wherein the surface of one filter element has a nitrogen-to-oxygen ratio in the range of from at least 0.01 to less than about 1.00 and/or the surface of the element is aminated relative to its bulk, and the surface of the other filter element is hydroxylated relative to its bulk, and obtaining a filtered plasma-rich biological fluid substantially free of leukocytes and platelets.

In some embodiments, the method includes passing biological fluid through the filter device without substantially activating complement in the biological fluid. For example, the level of the biologically active complement fragment C3a in the filtered fluid is not substantially increased as compared to the level in the fluid before filtration. In an embodiment, the method includes depleting the fluid of a biologically active complement fragment (e.g., C3a) upon passing it through the filter device.

Another embodiment of a method for processing a biological fluid comprises passing a leukocyte-containing plasma-rich biological fluid through a filter device comprising a filter including a fibrous leukocyte depletion medium and a fibrous leukocyte and platelet depletion medium, and collecting a filtered plasma-rich biological fluid substantially free of platelets and leukocytes.

A method for processing a biological fluid according to another embodiment comprises passing a leukocyte-containing plasma-rich biological fluid through a filter device comprising a filter including a fibrous leukocyte depletion medium and a fibrous leukocyte and platelet depletion medium, and collecting a filtered plasma-rich biological fluid substantially free of leukocytes, and C3a.

The invention also provides a method for processing a biological fluid comprising passing a leukocyte-containing plasma-rich biological fluid through a filter device comprising a filter including a fibrous leukocyte depletion medium and a fibrous leukocyte and platelet depletion medium, wherein the filter is arranged to substantially prevent the passage of red blood cells therethrough, and collecting a filtered plasma-rich biological fluid substantially free of platelets, leukocytes, and red blood cells.

In accordance with yet another embodiment of the invention, a method for processing a biological fluid is provided comprising passing a platelet-poor plasma-rich biological fluid through a filter device comprising a filter including a fibrous leukocyte depletion medium and a fibrous leukocyte and platelet depletion medium, and collecting a filtered plasma-rich biological fluid substantially free of platelets and leukocytes.

In some embodiments of the method, a filtered substantially cell-free plasma-containing fluid is provided, wherein the fluid is substantially free of C3a.

A system according to an embodiment of the invention comprises a filter device, and at least one container such as a plastic blood bag, in fluid communication with the filter device. Typical embodiments of the system include a filter device, interposed between, and in fluid communication with, at least two containers such as plastic blood bags. In one preferred embodiment, the system comprises a closed system.

As used herein, the term "complement" includes at least one of a complement protein, complement component (e.g., C1 through C9), complement fragment, biologically active fragment of a component (and metabolite of the fragment), complement factor (e.g., factor B and factor D), complement subcomponent, and complement complex (e.g., $\overline{C567}$). Exemplary biologically active fragments and metabolites thereof include C3a, C3a des Arg[77], C4a, C4a des Arg, C5a, and C5a des Arg.

As used herein, a biological fluid includes any treated or untreated fluid associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, components obtained from plasma, packed red cells (PRC), transition zone material or buffy coat (BC); blood products derived from blood or a blood component or derived from bone marrow; red cells separated from plasma and resuspended in a physiological fluid or a cryoprotective fluid; and platelets separated from plasma and resuspended in a physiological fluid or a cryoprotective fluid. The biological fluid may have been treated to remove some of the leukocytes before being processed according to the invention. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation. Typically, the volume of a unit varies, the amount differing from donation to donation. Multiple units of some blood components, particularly platelets and buffy coat, may be pooled or combined, typically by combining four or more units.

As used herein, the term "closed" refers to a system that allows the collection and processing (and, if desired, the manipulation, e.g., separation of portions, separation into components, filtration, storage, and preservation) of biological fluid, e.g., donor blood, blood samples, and/or blood components, without the need to compromise the integrity of the system. A closed system can be as originally made, or result from the connection of system components using what are known as "sterile docking" devices. Illustrative sterile docking devices are disclosed in U.S. Pat. Nos. 4,507,119, 4,737,214, and 4,913,756.

Each of the components of the invention will now be described in more detail below, wherein like components have like reference numbers.

In accordance with the invention, a filter device comprises a housing having an inlet and an outlet, and defining a fluid flow path between the inlet and the outlet, wherein a filter comprising at least one filter element is disposed across the fluid flow path. FIGS. 1-3 illustrated several embodiment of the filter device 100, comprising a housing 25 having an inlet 20 and an outlet 30, and defining the fluid flow path between the inlet and the outlet, wherein a filter 10, comprising at least one first filter element 1 and at least one second filter element 2, is disposed across the fluid flow path. FIG. 1 illustrates a filter 10 comprising a first filter element 1 and a second filter element 2, while FIGS. 2 and 3 illustrate filters having a plurality of first filter elements or second filter elements. In other embodiments (not shown) the filter comprises at least one filter element.

In accordance with the invention, the filter 10 is arranged to prevent the passage therethrough of an undesirable level of leukocytes, and typically, to prevent the passage of an undesirable level of platelets. In a preferred embodiment, the filter is arranged to prevent the passage therethrough of an undesirable level of red blood cells. Even more preferably, the filter is arranged to substantially remove at least one biologically active complement fragment such as C3a, and/or to substantially minimize activation of the complement fragment.

The filter 10 may be configured to remove a desired amount of leukocytes.

Typically, the filter is configured to remove greater than about 90%, preferably, greater than about 99%, even more preferably, greater than about 99.9%, or more, of the leukocytes from the plasma-rich fluid passing through the filter. For example, the filter can be configured to provide a filtered fluid having about $1 \times 10^4$ leukocytes or less. In some embodiments, the filter can be configured to provide a filtered fluid having about $1 \times 10^3$ leukocytes or less. In one embodiment, wherein the fluid to be filtered comprises platelet-poor-plasma, the resultant filtered fluid has about 200 leukocytes/liter or less, preferably, about 100 leukocytes/liter or less. In some embodiments, the filtered fluid has about 75 leukocytes/unit (e.g., wherein a unit has volume of about 300 ml) or less.

Typically, the filter is configured to prevent the passage therethrough of a significant level of platelets, and can be configured to prevent the passage therethrough of a substantial number of red blood cells. The filter can also be configured to reduce the passage therethrough of blood cell fragments.

Illustratively, the filtered fluid (e.g., in the container downstream of the filter) preferably contains less than about 5000 platelets/μL. For example, the resultant unit of filtered fluid can have less than about $1 \times 10^9$ platelets. In one preferred embodiment, the resultant unit of filtered fluid has about $1 \times 10^4$ platelets, or less, or about $1 \times 10^3$ platelets, or less. Preferably, there should be no visible indication (to the technician carrying out the filtration) of red blood cells downstream of the filter.

Preferably, the filter substantially minimizes activation of at least one complement fragment, e.g., a biologically active complement fragment such as C3a, in the biological fluid and/or removes at least one complement fragment from the biological fluid.

With respect to minimizing activation of at least one complement fragment, in an embodiment, the filtered fluid has a C3a level substantially similar to the C3a level in the unfiltered fluid, e.g., of about 900 ng/ml or less, in some embodiments, about 750 ng/ml or less.

With respect to depleting complement, the fluid can be filtered to provide a desired level of complement depletion. For example, in an embodiment, a biological fluid having a C3a level in the range of about 750 to about 900 ng/ml can be filtered to provide a fluid having a C3a level of about 500 ng/ml or less, in some embodiments, about 250 ng/ml or less.

The filter is arranged to filter a suitable volume of fluid in a suitable amount of time. For example, the filter can be capable of filtering about 200 to about 1000 ml of fluid without a significant effect on the overall processing time.

Illustratively, in some embodiments, the filter is capable of filtering about 250 to about 350 ml of fluid in about 15 minutes, or less, e.g., in about 10 minutes or less. In one embodiment, the filter is capable of filtering about 250 to about 350 ml of fluid in about 6 minutes.

In some other embodiments, the filter is capable of filtering about 500 to about 1000 ml of fluid in about 25 minutes, or less, preferably, about 20 minutes or less. In one embodiment, the filter is capable of filtering about 600 to about 850 ml of fluid (e.g., a unit of apheresed plasma) in about 18 minutes or less.

Preferably, one or more filter elements, e.g., each of the first element and the second element 1, 2 of the filter 10, typically comprising depth filter elements, comprise leukocyte depletion media, wherein at least some of the leukocytes are removed by adsorption. In some embodiments, the element, or the first and/or second element ,also remove at least some of the leukocytes by filtration (e.g., sieving). If desired, at least one element removes red blood cells by filtration.

A variety of materials can be used, including synthetic polymeric materials, to produce the porous media of the filter elements according to the invention. Suitable synthetic polymeric materials include, for example, polyolefins, polyesters, and polyamides. Illustrative suitable materials include polybutylene terephthalate (PBT), polyethylene, polyethylene terephthalate (PET), polypropylene, polymethylpentene, polyvinylidene fluoride, polyethersulfone, and nylon, such as nylon 6, nylon 66, nylon 612, nylon 11, and nylon 6 copolymers.

In one preferred embodiment, at least one element, e.g., the first element 1, and the second element 2, each comprise a fibrous medium, typically a fibrous polymeric medium prepared from melt-blown fibers, as disclosed in, for example, U.S. Pat. Nos. 4,880,548; 4,925,572, 5,152,905, 5,258,127, 5,443,743, and 5,472,621, as well as International Publication Nos. WO 91/04088, WO 93/04763, and WO 96/03194. An element, which can comprise a preformed medium, can include a plurality of layers and/or media.

One or more elements, e.g., first element 1 and/or the second element 2, can be treated for increased efficiency in processing a biological fluid. For example, surface characteristics of the first and/or second element can be modified (e.g., to affect the CWST, to include a surface charge, e.g., a positive or negative charge, and/or to alter the polarity or hydrophilicity of the surface) by chemical reaction including, for example, wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, heat, a Van der Graff generator, ultraviolet light, electron beam, or to various other forms of radiation, or by surface etching or deposition using a plasma treatment. The materials used to produce the elements can be treated before fabricating the elements, or the elements can be fabricated and subsequently treated.

Illustratively, any one or more of the elements may be surface modified to affect the critical wetting surface tension (CWST), as described in, for example, the U.S. Patents and International Publications listed above.

Typically, the first element 1 and the second element 2 each have a CWST of at least about 55 dynes/cm, more typically, at least 58 dynes/cm. Preferably, the first element 1 and the second element 2 each have a CWST of at least about 62 dynes/cm. The CWST of one element (e.g., the first element) can be different than the CWST of another element (e.g., the second element). Illustratively, one of the elements can have a CWST in the range of from about 58 dynes/cm to about 75 dynes/cm, and another element can have a CWST in the range of from about 78 dynes/cm to about 115 dynes/cm.

Preferably, at least one of the elements (e.g., the first element or the second element) has a CWST of greater than about 70 dynes/cm. For example, the element may have a CWST in the range from about 75 dynes/cm to about 115 dynes/cm, e.g., in the range of about 80 to about 100 dynes/cm. In some embodiments, the element has a CWST of about 85 dynes/cm, or greater, e.g., in the range from about 90 to about 105 dynes/cm, or in the range from about 85 dynes/cm to about 98 dynes/cm.

In those embodiments including a plurality of elements, while both the first and second elements preferably comprise leukocyte depletion media, the elements typically differ with respect to levels or efficiencies of platelet removal, as well as complement removal and/or inactivation.

For example, the first element typically comprises a platelet depletion medium, and the second element typically removes biologically active complement fragments such as C3a and/or does not substantially activate such biologically active complement fragments. Typically, as will be described in more detail below, the surface of the first element has a nitrogen-to-oxygen ratio in the range of from at least about 0.01 to less than about 1.00, and the second element has an hydroxylated surface.

In some embodiments, the first element (comprising a platelet depletion medium) comprises a medium that has been surface modified by exposure to gas plasma. The plasma can be generated by any suitable method, preferably, by electrical discharge, e.g., radio frequency (RF) discharge. The gas used to treat the surface of the medium can include one or more inorganic and/or organic gases. Illustrative inorganic gases include helium, argon, nitrogen, neon, nitrous oxide, nitrogen dioxide, oxygen, air, ammonia, carbon monoxide, carbon dioxide, hydrogen, chlorine, hydrogen chloride, bromine cyanide, sulfur dioxide, hydrogen sulfide, xenon, krypton, and the like. Illustrative organic gases include acetylene, pyridine, gases of organosilane compounds and organopolysiloxane compounds, fluorocarbon compounds, and the like. In addition, the gas can be a vaporized organic material, such as an ethylenic monomer to be plasma polymerized or deposited on the surface of the medium. These gases may be used either singly, or as a mixture of two kinds (e.g., two inorganic gases, two organic gases, and inorganic gas and an organic gas) or more. For example, the atmosphere where plasma is generated can includes a carrier gas, e.g., helium or argon.

In some preferred embodiments, the medium is exposed to a gas plasma generated in an atmosphere comprising a nitrogen-containing molecule to obtain a plasma treated substrate. Any suitable nitrogen-containing molecule can be used, one preferred nitrogen-containing molecule is ammonia. As noted above, the atmosphere where plasma is generated can include a carrier gas.

Examples of other nitrogen-containing molecules include alkylamines, allylamines, alkylimines, ethanolamines, hydroxylamines, nitro compounds such as, for example, nitroalkanes, and amides such as, for example, formamide and acetamide.

In one preferred embodiment, surface of the first element has a nitrogen-to-oxygen ratio in the range of from at least about 0.01 to less than about 1.00. In a more preferred embodiment, the nitrogen-to-oxygen ratio is in the range of from at least about 0.02 to less than about 1.00. In some embodiments, the surface of the first element is substantially non-hydroxylated, e.g., having less than about 0.1% hydroxyl groups (less than about 1000 ppm).

Alternatively, or additionally, in an embodiment, the first element has a surface characterized by one or more, and in some embodiments, two or more, of the following: a surface that is hydroxylated (has more hydroxyl groups) relative to its bulk, i.e., the surface is more hydroxylated than the interior portion of the element adjacent or under the surface and/or is more hydroxylated than the substrate of the element; a surface that is aminated (has more amine groups) relative to its bulk; a surface that has a greater number of carbonyl groups relative to its bulk; a surface that has a greater number of carboxyl groups relative to its bulk; a surface that has more ether groups relative to its bulk; and a surface that has more amido groups relative to its bulk.

Illustrative gases and gas plasma treatments include those disclosed in, for example, U.S. Pat. Nos. 5,258,127, 5,443,743, 5,679,264, as well as in International Publication Nos. WO 93/04763 and WO 96/03194.

In some embodiments, the filter element that removes biologically active complement fragments such as C3a and/or does not substantially activate such biologically active complement fragments (i.e., the second element) comprises a medium that has been treated (e.g., surface modified) to include a high density of hydroxyl groups, more preferably, to also include anionic groups, e.g., some carboxyl groups as well as the high density of hydroxyl groups.

For example, the second element can have a hydroxylated surface, and in an embodiment, has a grafted coating comprising hydroxyl groups, e.g., comprising an hydroxylated polymer, such as, but not limited to, an hydroxyl acrylate polymer. In some embodiments including a hydroxylated polymer, the polymer further comprises carboxyl groups, e.g., a copolymer including a hydroxyl-containing monomer and a carboxyl containing monomer, such as, but not limited to, a copolymer of hydroxyalkylacrylate and acrylic acid.

In an exemplary technique, at least one of a variety of monomers each comprising an ethylene or acrylic moiety and a second group, which can be selected from hydrophilic groups (e.g., —COOH, or —OH) are used, e.g., in radiation grafting. Grafting of the medium can also be accomplished by compounds containing an ethylenically unsaturated group, such as an acrylic moiety, combined with a hydroxyl group, e.g., monomers such as hydroxyethyl methacrylate (HEMA) or acrylic acid. The compounds containing an ethylenically unsaturated group may be combined with a second monomer such as methacrylic acid (MAA). In an embodiment, the medium is surface modified using a mixture including hydroxyl-terminated and carboxyl-terminated monomers.

Illustrative compounds and groups, e.g., hydroxyl groups and carboxyl groups, as well as illustrative medium treatment protocols include, but are not limited to, those disclosed in U.S. Patent Nos. 5,152,905, 4,880,548 and 4,925,572, as well as International Publication No. WO 91/04088.

In some embodiments, one or more elements, and typically, both the first and second filter elements, has a negative zeta potential at physiological pH (e.g., about 7 to about 7.4).

For example, the filter element comprising a platelet depletion medium can have a zeta potential of about −3 millivolts (mv), at physiological pH, or the zeta potential can be more negative, e.g., in the range of from about −5 mv to about −25 mv. embodiments, the platelet depletion medium has a zeta potential in the range from about −8 mv to about −20 mv at physiological pH.

The filter element comprising a medium that removes biologically active complement fragments and/or does not substantially activate the fragments can have can have a zeta potential of about−−3 millivolts (mv) at physiological pH, or the zeta potential can be more negative, e.g., in the range of from about −5 mv to about −20 mv. In some embodiments, the medium has a zeta potential in the range from about −7 mv to about −15 mv at physiological pH.

In some embodiments wherein both types of media have a negative zeta potential at physiological pH, one medium can have a zeta potential that is more negative than that of the other medium.

Typically, the filter has a pore structure that reduces the passage therethrough of white and/or red blood cells. The pore structure can be characterized in terms of pore size, which may be determined by a variety of techniques known to the ordinary artisan. Illustratively, the pore structure can refer to the pore rating or pore diameter as measured by, for example, the modified F2 test, e.g., as described in U.S. Pat. Nos. 4,925,572 and 5,229,012. The pore structure can refer to an average pore size as measured by, for example, a Coulter Instruments porometer (e.g., a Coulter Porometer II® machine). Other suitable techniques for determining pore structure values include bubble point tests and Latex Sphere Tests.

For example, the filter can have a pore diameter of about 8 micrometers (μm) or less. In another embodiment, the filter and/or at least one filter element has a pore diameter of about 5 micrometers or less. In another embodiment, the filter has a pore diameter of about 2.5 micrometers, or less.

The filter can include a plurality of filter elements having different pore structures and/or at least one element can have a varied pore structure.

Typically, each of the types of media has a voids volume of at least about 70%, more preferably, at least 75%. In one embodiment, each of the types of media has a voids volume of about 80% or more. In some embodiments, each of the types of media has a voids volume in the range of from about 85% to about 96%. Typically, in those embodiments wherein the filter includes two or more elements forming a laminate, the laminate has a voids volume in the range of from about 75% to about 85%.

In accordance with the invention, the filter can include a plurality of first elements and/or second elements, arranged in a variety of configurations. Illustratively, FIGS. 1-3 show exemplary configurations, wherein at least a portion of the filter 10 has alternating elements. In some embodiments, the first and second elements can alternate, or there can be two or more first elements followed by one or more second elements, and/or other combinations. For example, a portion of the filter can include alternating elements, and at least another portion of the filter can include a plurality of the same type of element.

Either element can be the most upstream (e.g., closest to the inlet of the filter device) or downstream (e.g., closest to the outlet). Alternatively, the most upstream and downstream element can be the same (e.g., the second element), with the other type of element (e.g., the first element) interposed between the upstream and downstream elements.

The filter 10 can include additional elements, layers, or components, that can have different structures and/or functions, e.g., at least one of prefiltration, support, drainage, spacing and cushioning. Illustratively, the filter can also include at least one additional element such as a mesh and/or a screen.

The filter 10, comprising the first and second elements, is typically placed in a housing 25 to form a filter assembly or filter device 100. Preferably, the filter device is sterilizable. Any housing of suitable shape to provide an inlet and an outlet may be employed. The housing is preferably fabricated from any suitable impervious material, including any impervious thermoplastic material, which is compatible with the fluid being processed. The housing may include an arrangement of one or more channels, grooves, conduits, passages, ribs, or the like, which may be serpentine, parallel, curved, circular, or a variety of other configurations.

Suitable exemplary housings are disclosed in U.S. Pat. Nos. 5,100,564, 5,152,905, 4,923,620, 4,880,548, 4,925,572, and 5,660,731, as well as International Publication No. WO 91/04088. It is intended that the present invention not be limited by the type, shape, or construction of the housing.

Typically, the filter device or filter assembly 100 according to the invention is included in a biological fluid processing system, e.g., a system including a plurality of conduits and containers, preferably flexible containers such as blood bags. In one preferred embodiment, a system according to the invention comprises a closed system including the filter device.

Figure 6:
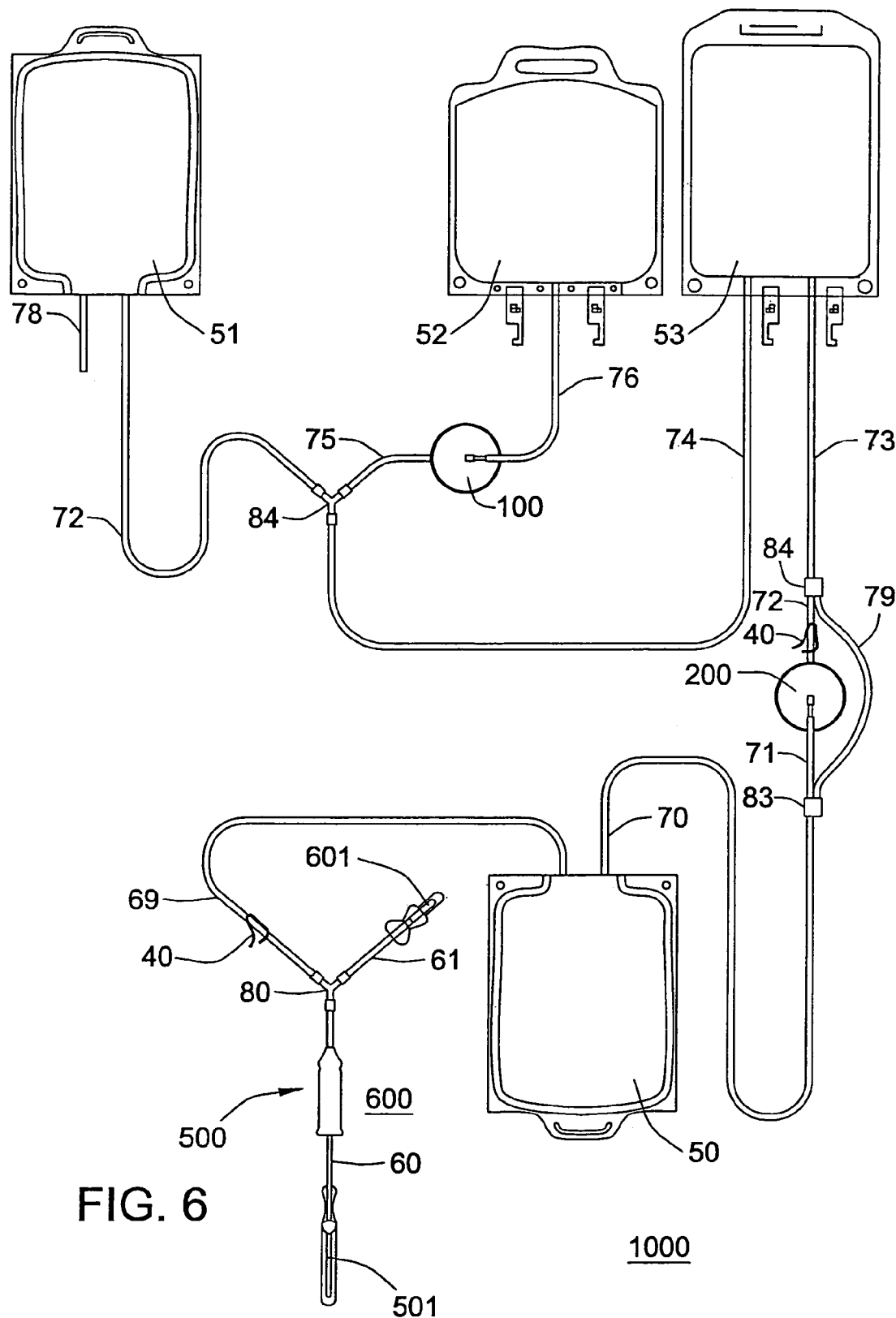
FIG. 6 is another embodiment of a biological fluid processing system including a filter device according to the invention.

FIGS. 4 and 6 illustrate exemplary embodiments of a biological fluid processing system 1000, including the filter device 100 and a plurality of containers 50-53, wherein the components of the system are in fluid communication with each other via a plurality of conduits and connectors, e.g., conduits 60-79 and 91-96, and connectors 80-84. Typically, the system includes at least one, and more typically, at least two flow control devices such as clamps, valves, and/or transfer leg closures. For example, the embodiment illustrated in FIG. 4 includes a flow control device 40 and the embodiment illustrated in FIG. 6 includes two flow control devices 40. In a variation of the system illustrated in FIG. 4, additional flow control devices such as clamps and/or transfer leg closures are associated with conduits 63, 65, and 67. In a variation of the system illustrated in FIG. 6, additional flow control devices such as clamps and/or transfer leg closures are associated with conduits 70, 74, and 72.

In both of these illustrated embodiments, the system 1000 also includes a phlebotomy needle 501 (with a cover), a phlebotomy needle protector 500 (e.g., having at least a flexible side wall and being capable of sliding along a conduit and retaining the phlebotomy needle therein as described in International Publication No. WO 00/06229), a sampling arrangement 600, a sampling arrangement needle or cannula 601 (with a cover), and an additional filter device, leukocyte filter device 200. In those embodiments including a sampling arrangement 600, the arrangement is preferably disposed to minimize contamination of the collected biological fluid by allowing a first sample or portion of the collected fluid (that may be more susceptible to contamination) to be passed to a location other than the collection container 50 (e.g., as described in International Publication Nos. WO 00/07642 and WO 98/28057). For example, the first sample is passed from phlebotomy needle 501 through the sampling arrangement 600 and sampling arrangement needle 601 into a sampling device (not shown) such as an evacuated stoppered collection device. In other embodiments (not shown) the sampling arrangement does not include a needle or cannula, and allows portions or samples of fluid to be passed into one or more attached containers or reservoirs while maintaining a closed system. After the first portion of fluid is passed through the sampling arrangement, a second portion of fluid (that may be less susceptible to contamination) can be collected in the collection container.

One or more containers in the system can be suitable for holding, for example, blood components and/or additives (e.g., nutrients, storage solutions, and/or inactivation agents). The system can include additional components, such as, for example, additional filter devices, including leukocyte depletion filter devices, (with and without filter bypass loops). Additionally, or alternatively, the system can include at least one of the following: a vent such as a gas collection and displacement arrangement, one or more gas inlets, one or more gas outlets, at least one flow control device such as a clamp, transfer leg closure or valve, as well as a sampling arrangement, one or more needles and/or cannulas, and a phlebotomy needle protector.

In the embodiments of the system 1000 illustrated in FIGS. 4 and 6, the system includes leukocyte filter device 200, e.g., to reduce the level of leukocytes from a red blood cell-containing biological fluid (e.g., packed red blood cells or whole blood). The red blood cell-containing fluid can be further processed.

For example, in accordance with one embodiment of the system illustrated in FIG. 4, a unit of biological fluid, e.g., a unit of whole blood, is passed through phlebotomy needle 501 along conduits 60 and 62 into collection bag 50, that typically contains an additive such as an anticoagulant. If desired, a first portion of biological fluid can be passed through the sampling arrangement 600 before collecting the unit of biological fluid. For example, a first portion of blood can be passed through phlebotomy needle 501, and along conduit 60, connector 80, conduit 61, and through needle 601 into a sampling device. Alternatively, the sampling arrangement can include at least one container or reservoir rather than a needle, and the portion(s) can be passed into the container or reservoir. In another embodiment, the portion of blood is passed through the sampling arrangement after collecting the unit of biological fluid.

Continuing to use the illustrative system shown in FIG. 4 for reference, the unit of biological fluid is typically centrifuged to provide a supernatant layer comprising a plasma-rich fluid (e.g., platelet-poor-plasma), a sediment layer comprising red blood cells, and a buffy coat layer between the supernatant and sediment layers. Alternatively, the unit of blood is centrifuged to provide a supernatant layer comprising plasma-rich fluid, and a sediment layer comprising red blood cells.

Subsequently, the plasma-rich fluid (e.g., platelet-poor plasma) is passed from the collection container 50 along conduits 63 and 64 into first satellite container 51 through the filter device 100, i.e., the device comprising a filter 10 having first and second filter elements 1 and 2 as described above, to provide plasma-rich fluid substantially free of leukocytes and platelets without externally visible red blood cells in first satellite container 51. In an embodiment, the filtered plasma-rich fluid is also substantially free of at least one biologically active complement fragment such as C3a.

The separated blood components can be further processed if desired. For example, in accordance with the embodiment of the system illustrated in FIG. 4, the sediment layer (comprising red blood cells) can be passed along conduit 65 into second satellite container 52, and subsequently passed along conduit 66, through leukocyte filter device 200 and along conduit 67 into third satellite container 53. In some embodiments, different blood components can be passed essentially simultaneously from separate ports of the collection bag 50, for example, along conduit 63 (e.g., plasma-rich fluid) and conduit 65 (red blood cell-rich fluid).

If desired, the red blood cells can be combined with an additive solution (before or after filtration). After filtration, the red cells, or the red cells combined with additive solution, can be stored until needed.

In accordance with an embodiment of the system illustrated in FIG. 6, a unit of whole blood can be passed through phlebotomy needle 501 along conduits 60 and 69 into collection bag 50, that typically contains an additive such as an anticoagulant. If desired, one or more portions of biological fluid can be passed through the sampling arrangement 600 as described with respect to FIG. 4.

The biological fluid is subsequently passed into satellite container 53 along conduit 70, connector 82, and conduit 71, through leukocyte filter device 200 (in some embodiments, a leukocyte- and platelet-depleting filter device that allows red cells and plasma to pass therethrough), along conduit 72, connector 83, and conduit 73. If desired, any embodiments of a system can include additional components such as at least one vent, e.g., a gas inlet and or a gas outlet, or include a bypass loop and/or a gas displacement loop. For example, FIG. 6 shows a bypass loop communicating with the filter device 200 (e.g., comprising conduit 79, and a check valve (not shown) between the ends of the loop).

Preferably, the biological fluid in satellite container 50 is centrifuged to provide a supernatant layer comprising plasma-rich fluid (e.g., platelet-poor-plasma) and a sediment layer comprising red blood cells, and the supernatant layer of plasma rich fluid is passed through filter device 100 (i.e., containing filter 10) into satellite container 52 along conduit 74, connector 84, conduit 75, and conduit 76. In some embodiments, satellite container 51 contains a red blood cell additive solution, that is subsequently passed from container 51 into satellite bag 53, containing red blood cells therein. If desired, the red blood cells, typically combined with additive solution, can be stored until needed.

FIGS. 5A and 5B illustrate other embodiments of a biological fluid processing system including filter device, and at least one first satellite container suitable for receiving the filtered fluid passing through the filter device. Accordingly, FIG. 5A shows filter device 100 and a downstream first satellite container 51, in fluid communication via conduits 90 and 91, and FIG. 5B shows filter device 100 and two first satellite containers 51a and 51b, in fluid communication via conduits 92-95 and connector 81. The embodiments illustrated in FIGS. 5A and 5B are especially suitable for attachment (for example, via sterile docking) to other biological fluid processing systems, e.g., including collection and/or satellite bags (including wet bag systems) and/or apheresis systems.

The embodiment illustrated in FIG. 5B (i.e., including two first satellite containers 51a and 51b) is especially useful for use with some apheresis systems, for example, those systems that provide for collecting two units of biological fluid.

In exemplary variations of the system illustrated in FIG. 4, the system does not include leukocyte filter device 200 and third satellite container 53, or the system includes third satellite container 53 but does not include leukocyte filter device 200. However, if desired, the additional system component(s) can be added, e.g., via sterile-docking.

EXAMPLE 1

A system is arranged as generally shown in FIG. 4.

A filter comprising 6 first filter elements and 5 second filter elements is placed in a housing to provide a filter device. The first and second filter elements alternate, to provide a filter having 11 layers. The first filter element is utilized for layers 1, 3, 5, 7, 9, and 11, and the second filter element is utilized for layers 2, 4, 6, 8, and 10. Each filter element is a planar circular disc having a diameter of about 47 mm.

The 11 layers are uncompressed, and the resultant filter has an average voids volume of about 91%.

The first filter element and second filter element each comprise melt-blown PBT fibers.

The first filter element, comprising a leukocyte depletion medium, wherein the element does not substantially activate C3a, is surface modified in accordance with U.S. Pat. No. 4,880,548, and has a CWST of 95 dynes/cm, and a negative zeta potential at a pH of about 7.1.

The second filter element, comprising a leukocyte depletion medium wherein the element substantially removes platelets, is surface modified with gas plasma in accordance with U.S. Pat. No. 5,258,127, and has a CWST of 65 dynes/cm, and a negative zeta potential at a pH of about 7.1.

Units of whole blood are collected in collection bags containing citrate-phosphate-dextrose preservative, i.e., CPD or CP2D. Each collection bag has a top port and a bottom port. The collection bag containing the blood therein is centrifuged to provide three fractions of blood components, i.e., a sediment layer comprising concentrated red blood cells, an intermediate layer comprising the "buffy coat," and a supernatant layer comprising platelet-poor-plasma (PPP).

The collection bag is placed in a plasma expresser and the PPP is expressed from the top port of the collection bag, through the filter device, and into an empty satellite bag. Red blood cells are not visible in the fluid passing into the satellite bag. Flow is stopped when about 50 ml of plasma remain in the bag, e.g., before the buffy coat is passed into the satellite bag. The filtration time is about 6 minutes.

Analysis of the unit of filtered PPP shows less than 57 white cells in the total volume of PPP (corresponding to less than about 200 white blood cells per liter). There are less than about 650 platelets/µL present.

The C3a concentration in the filtered PPP is below the detection limit of the assay, that is 137.5 ng/ml.

This example shows that filter devices according to the invention can provide substantially leukocyte-free and substantially C3a-free plasma.

EXAMPLE 2

Filter devices are provided as described in Example 1. Units of apheresed plasma are obtained, and filtered within approximately 1 hour of collection. The average volume of the units is about 650 ml. The filter device is interposed between the bag containing the unit of apheresed plasma, and an empty satellite bag, and the plasma-containing bag and the filter device are arranged to allow gravity filtration, with a head height of 60 inches.

The average filtration time is 16 minutes. Analysis of the filtered plasma shows the average leukocyte residual is $1.8 \times 10^4$ white blood cells per unit, and the average platelet residual is $1.8 \times 10^9$ platelets per unit. The C3a concentration in the filtered plasma is below the detection limit of the assay.

This example shows that filter devices according to the invention can filter a unit of apheresed plasma in a suitable amount of time while providing substantially leukocyte-free and substantially C3a-free plasma.

EXAMPLE 3

A filter is configured having 11 layers of PBT as described in Example 1. The first filter element, having 6 layers, is surfaced modified by treatment with hydroxyethyl methacrylate (HEMA) and methacrylic acid (MAA), as generally disclosed in U.S. Pat. No. 4,880,548.

The second filter element, having 5 layers, is surface modified by treatment with a mixture of argon and ammonia gas plasma as generally disclosed in U.S. Pat. No. 5,258,127.

Samples of unmodified PBT, and samples from the first and second elements are analyzed by X-ray photoelectron spectroscopy (XPS), using a Physical Electronics 5700LSci ESCA spectrometer. The X-ray source is monochromatic aluminum, the source power is 350 watts, the exit angle (the angle between the surface plane and the electron analyzer lens) is 50°, and the charge correction is C-(C,H) in C 1s spectra at 284.6 eV.

The concentration of elements detected (in Atom %) are shown below in Table I, and the summary of carbon functional groups (in Atom % Carbon) are shown below in Table II.

TABLE I

Concentration of Elements Detected (in Atom %)

| sample | O | N | C | Si |
|---|---|---|---|---|
| unmodified | 23.7 | 0.2 | 76.1 | 0.1 |
| HEMA/MAA | 28.0 | 0.5 | 71.4 | 0.0 |
| gas plasma | 18.8 | 3.1 | 78.0 | 0.1 |

TABLE II

Summary of Carbon Functional Groups (in Atom % Carbon)

| | C—(C,H) | | C—(O,N)@ | | C=O# | | (O,N)—C=O$ | |
|---|---|---|---|---|---|---|---|---|
| sample | B.E.+ | atom % C | B.E.+ | atom % C | B.E.+ | atom % C | B.E.+ | atom % C |
| unmod* | 284.6 | 54 | 286.0 | 11 | — | — | 288.5 | 10 |
| HEMA/MAA | 284.6& | 49 | 286.1 | 12 | 287.2 | 3 | 288.5 | 5 |
| gas plasma | 284.6 | 58 | 286.1 | 13 | — | — | 288.4 | 7 |

+binding energy
@alcohol, ether, amine
ketone, aldehyde
$ester, carboxylic acid, amide
*also contained about 1 atomic % aromatic carbon (e.g., phenyl, benzyl)
&the C—(C,H) peak is a combination of two peaks The data shows that an embodiment of a filter according to the invention has a first element having a surface that is hydroxylated relative to its bulk, and a second element having a surface having a nitrogen-to-oxygen ratio of 0.017.

EXAMPLE 4

A filter is prepared as described in FIG. 3, i.e., the first and second filter elements (comprising melt-blown PBT) alternate, to provide a filter having 11 layers. The first filter element is utilized for layers 1, 3, 5, 7, 9, and 11, and the second filter element is utilized for layers 2, 4, 6, 8, and 10. Each filter element is a planar circular disc having a diameter of about 47 mm. The first filter element has a CWST of 95 dynes/cm and a zeta potential of −8 mv at a pH of 7.0. The second filter element has a CWST of 65 dynes/cm, and a zeta potential of −10 mv at a pH of 7.0.

The average fiber diameter of the fibers in each element is about 2.7 micrometers.

The 11 layers are calendered together utilizing heat compression on a continuous belt. The resultant laminate filter has an average voids volume of about 79%, and a pore diameter of about 2 micrometers.

Units of whole blood (about 450 mL) are collected, and centrifuged, as generally described in Example 1. Using head heights of 100 cm or 150 cm (equal numbers of units of platelet-poor-plasma are filtered at the two head heights), platelet-poor-plasma is passed through the filter devices, and flow is stopped before buffy coat passes from the collection container. The filtration times average less than 5 minutes.

Analysis of the filtered fluid shows, on the average, less than 150 white blood cells per unit of PPP (corresponding to less than 500 white blood cells per liter). On the average, there are less than $5 \times 10^9$ platelets per unit. The C3a concentration of the filtered plasma is below the detection limit of the assay.

This example shows filter devices according to an embodiment of the invention can be used to provide substantially leukocyte-, platelet- and C3a-free plasma via gravity filtration.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A method for processing a biological fluid comprising: passing a biological fluid through a filter device comprising a filter comprising at least two fibrous filter elements wherein the surface of one filter element is substantially non-hydroxylated and has a nitrogen-to-oxygen ratio in the range of from at least 0.01 to less than about 1.00, and the surface of the other filter element is hydroxylated relative to the bulk of the element, wherein the filter elements have a negative zeta potential at physiological pH; and obtaining the filtered fluid.

2. A method for processing a biological fluid comprising: passing a leukocyte-containing plasma-rich fluid through a filter comprising at least two filter elements, wherein the surface of one filter element is substantially non-hydroxylated and has a nitrogen-to-oxygen ratio in the range of from at least 0.01 to less than about 1.00, and the surface of the other filter element is hydroxylated relative to the bulk of the element wherein the filter elements have a negative zeta potential at physiological pH; and
obtaining a filtered plasma-rich biological fluid substantially free of leukocytes and platelets.

3. The method for processing a biological fluid according to claim 2, wherein passing the leukocyte-containing plasma-rich biological fluid through the filter comprising passing the fluid through at least one additional filter element, wherein at least a portion of the surface of the element is aminated relative to the bulk of the element, and another portion of the surface of the element is hydroxylated relative to the bulk of the element.

4. The method for processing biological fluid according to claim 2, wherein passing the leukocyte-containing plasma-rich fluid through the filter comprises passing the fluid through at least two additional filter elements, the surface of one additional element being substantially non-hydroxylated and having a nitrogen-to-oxygen ratio in the range of from at least 0.01 to less than about 1.00, and the surface of the other additional element being hydroxylated relative to the bulk of the element.

5. The method of claim 2 wherein the filtered plasma-rich fluid is substantially free of C3a.

6. The method of claim 2 wherein the leukocyte-containing plasma-rich biological fluid comprises a platelet-poor biological fluid.

7. The method of claim 5, including collecting plasma-rich fluid in a downstream container without substantially activating C3a in the plasma-rich fluid.

8. The method of claim 2 wherein the two filter elements have different critical wetting surface tensions (CWSTs).

9. The method of claim 2 wherein at least one filter element has a critical wetting surface tension of at least about 90 dynes/cm.

10. The method of claim 2, comprising passing about 200 to about 1000 ml of leukocyte-containing plasma-rich fluid through the filter.

* * * * *